US009248215B2

(12) United States Patent
Barry et al.

(10) Patent No.: US 9,248,215 B2
(45) Date of Patent: Feb. 2, 2016

(54) INJECTABLE BONE VOID FILLER

(75) Inventors: John J. Barry, Vienna (AT); Andreas Goessl, Vienna (AT); Heinz Gulle, Enzersdorf (AT); Monika Mangold, Vienna (AT); Melitta Bilban, Vienna (AT)

(73) Assignees: Baxter International Inc., Deerfield, IL (US); Baxter Healthcare S.A., Glattpark (Opkifon) (CH)

( * ) Notice: Subject to any disclaimer, the term of this patent is extended or adjusted under 35 U.S.C. 154(b) by 379 days.

(21) Appl. No.: 11/736,500

(22) Filed: Apr. 17, 2007

(65) Prior Publication Data

US 2007/0276505 A1 Nov. 29, 2007

Related U.S. Application Data

(60) Provisional application No. 60/808,802, filed on May 26, 2006.

(51) Int. Cl.
*A61F 13/00* (2006.01)
*A61K 38/48* (2006.01)
*A61K 38/00* (2006.01)
*A61L 27/22* (2006.01)

(52) U.S. Cl.
CPC ............ *A61L 27/225* (2013.01); *A61L 2400/06* (2013.01); *A61L 2430/02* (2013.01)

(58) Field of Classification Search
USPC ............ 424/422, 94.64; 514/16.7, 13.8, 14.2, 514/14.7, 14.9, 16.8
See application file for complete search history.

(56) References Cited

U.S. PATENT DOCUMENTS

| | | | |
|---|---|---|---|
| 4,696,812 A | 9/1987 | Silbering et al. | |
| 5,242,683 A | 9/1993 | Klaveness | |
| 5,549,904 A * | 8/1996 | Juergensen et al. ............ | 424/423 |
| 5,752,974 A | 5/1998 | Rhee et al. | |
| 5,861,043 A | 1/1999 | Carn | |
| 6,096,309 A | 8/2000 | Prior et al. | |
| 6,287,341 B1 | 9/2001 | Lee et al. | |
| 6,605,294 B2 | 8/2003 | Sawhney | |
| 6,607,535 B1 | 8/2003 | Chan | |
| 6,703,038 B1 | 3/2004 | Schaefer et al. | |
| RE39,192 E | 7/2006 | MacPhee et al. | |
| 2001/0016646 A1* | 8/2001 | Rueger et al. ................. | 530/840 |
| 2002/0091411 A1* | 7/2002 | Saker ............... A61B 17/00491 | 606/213 |
| 2003/0194389 A1 | 10/2003 | Porter | |
| 2004/0048947 A1 | 3/2004 | Lidgren et al. | |
| 2004/0068266 A1* | 4/2004 | Delmotte ........................ | 606/92 |
| 2004/0101960 A1 | 5/2004 | Schaefer et al. | |
| 2005/0119746 A1 | 6/2005 | Lidgren | |
| 2005/0136038 A1 | 6/2005 | de Bruijn et al. | |
| 2006/0089715 A1 | 4/2006 | Truckai et al. | |
| 2006/0106364 A1 | 5/2006 | Whitlock et al. | |
| 2007/0275028 A1 | 11/2007 | Barry et al. | |
| 2008/0241072 A1 | 10/2008 | Barry et al. | |

FOREIGN PATENT DOCUMENTS

| | | | |
|---|---|---|---|
| EP | 0 166 263 | 1/1986 | |
| EP | 166263 A1 | 1/1986 | |
| JP | 60-256460 | 12/1985 | |
| JP | 07-213598 A | 8/1995 | |
| JP | WO 2006072623 A1 * | 7/2006 | ......... A61K 38/1875 |
| WO | WO 95/21634 | 8/1995 | |
| WO | WO 95/21634 A1 | 8/1995 | |
| WO | WO 97/15188 A1 | 5/1997 | |
| WO | WO 00/07639 | 2/2000 | |
| WO | WO 00/07639 A1 | 2/2000 | |
| WO | 03053488 | 7/2003 | |
| WO | WO 03/053488 | 7/2003 | |
| WO | 2004/078223 A1 | 9/2004 | |
| WO | 05/86697 | 9/2005 | |
| WO | 2006/005269 | 1/2006 | |
| WO | 2006/050268 | 5/2006 | |
| WO | WO 2006/007623 * | 7/2006 | ............. A61K 38/18 |
| WO | WO 2006/072622 A2 | 7/2006 | |
| WO | WO 2006/072623 A1 | 7/2006 | |
| WO | WO 2006/073711 A2 | 7/2006 | |

OTHER PUBLICATIONS

Jones, C.I. et al. Thrombosis Research vol. 112, pp. 65-71. Published 2003.*
Menovsky, T. et al. The Laryngoscope vol. 108, pp. 1390-1393. Published 1998.*
Omnipaque 300 Dosing indications (reference.medscape.com/drug/omnipaque-iohexol-343760).*
Omnipaque dosing instructions. Published 2010.*
Jones et al., (Thrombosis Research vol. 112, pp. 65-71, published 2003).*
Taylor (J. Bone Joint Surg. vol. 77 pp. 881-883, published 1999).*
Parikit, SN, "Bone Graft Substitutes: Past, Present, Future", 2002, *J Postgrad Med*, vol. 48, pp. 142-148.
International Search Report and Written Opinion for PCT/US2008/058146 mailed Oct. 15, 2009, 13 pgs.
International Preliminary Report on Patentability for for PCT/US2008/058146 mailed Oct. 29, 2009, 10 pgs.
Parikit, SN, "Bone Graft Substitutes: Past, Present, Future," 2002, *J. Postgrad Med*, vol. 48, pp. 142-148.
Achtari et al., Gynakol Geburtschilfliche Rundsch, 46:39-44 (2006) (Abstract).
Barth et al., JAVMA, 226(1):73-76 (2005).
Brown et al., Am. J. Pathol., 142(1):273-283 (1993).
Kneser, U., et al., "Fibrin gel-immobilized primary osteoblasts in calcium phosphate bone cement: In vivo evaluation with regard to application as injectable biological bone substitute," 2005, *Cells Tissues Organs*, vol. 179, pp. 158-169.
Le Guehennec, L., et al., "A review of bioceramics and fibrin sealant," 2004, *European Cells and Materials*, vol. 8, pp. 1-11.

(Continued)

*Primary Examiner* — Paul Zarek
*Assistant Examiner* — George W Kosturko
(74) *Attorney, Agent, or Firm* — Kilpatrick Townsend & Stockton LLP

(57) ABSTRACT

The present invention relates to a biodegradable fibrin based composition for injection into osseous defects or voids, which can be the result of osteoporosis, surgery, bone cysts, tumor removal or traumatic bone injury.

29 Claims, 3 Drawing Sheets

(56) References Cited

OTHER PUBLICATIONS

Trout, A.T., "New Fractures After Vertebroplasty: Adjacent Fractures Occur Significantly Soonr", 2006. *J. Neuroradiol*, vol. 27, pp. 217-223.

Wittkampf, Albert R.M., "Fibrin glue as cement for HA-granules," 1988, *J. Cranio-Max. Fac. Surg.*, vol.17, pp. 179-181.

Wittkampf, Albert R.M., "Augmentation of the maxillary alveolar ridge with hydroxylapatite and fibrin glue," 1989, *J. Oral Maxillofac. Surg.*, vol. 46, pp. 1019-1021.

Zhi et al., J. Long-Term Effects of Medical Implants, 15(4):375-388 (2005).

Isogai, et al., "Formation of Phalanges and Small Joints by Tissue-Engineering," The Journal of Bone and Joint Surger, Mar. 3, 1999, pp. 306-316, vol. 81-A, No. 3.

Jiashahood, "What is Viscosity?—My Process Engineers," My Process Engineers, Retrieved from http://www.myprocessengineers.com/2012/02/what-is-viscosity.html on Mar. 28, 2012, 2011, 3 pages.

* cited by examiner

INJECTABLE BONE VOID FILLER

FIELD OF THE INVENTION

The present invention relates to a biodegradable fibrin based composition (in the following also designated as "bone void filler composition" or "bone void filler") for injection into osseous defects or voids, which can be the result of osteoporosis, surgery, bone cysts, tumor removal or traumatic bone injury.

BACKGROUND OF THE INVENTION

There are several examples of injectable bone void fillers in the literature. WO 95/21634 discloses a biomaterial for the resorption substitution of bony tissue. The composition is injectable and comprises calcium phosphate particles in a liquid phase comprising carboxymethylcellulose. U.S. Pat. No. 6,287,341 details a method for repairing an osseous defect wherein two calcium phosphates are mixed with a buffer to provide a paste or putty which is applied to the defect. The putty hardens in the defect due to a chemical reaction. WO 00/07639 discloses a calcium cement for injection into osseous defects. The cement is based on mono basic calcium phosphate monohydrate and beta tricalcium phosphate and may further comprise a biopolymer. Following injection the calcium phosphate cement requires setting. US-patent 2004048947 details an injectable composition for a bone mineral substitute material with the capability of being hardened in a body fluid in vivo, which hardens during the surgery. US-patent 2004101960 details an injectable bone substitute material comprising a mix of living cells within a composition which comprises a soft matrix or a composition which comprises a setting material. The soft materials listed in this patent include collagen gels, gelatin, alginates, agarose, polysaccharides, hydrogels and viscous polymers. It is also mentioned that it is possible to employ commercial fibrin glues such as TissuCol (Baxter) or Beriplast (Aventis) but they are not preferred. Recently there have been a number of injectable bone void fillers that have received 510(k). Of these, Jax-TCP (Smith & Nephew) and Tricos T (Baxter) deliver granules of calcium phosphates in a bio-gel which are applied as a putty/paste.

The current practice is to fill bone voids with either a bone graft (auto or allograft), bone graft substitutes, a bone cement such as polymethylmethacrylate (PMMA) or injectable calcium salt void fillers. Autografts are the 'gold standard' choice for this application but there are issues with donor tissue limitations, trauma, infection and morbidity. There are a number of additional problems that face allografts, including the risk of disease transmission and immunogenicity. Both auto- and allografts display loss of biological and mechanical properties due to secondary remodeling. It is these limitations that have prompted interest in alternative materials to bone grafts (Parikh S. N., 2002, J. Postgrad. Med. 48:142-148).

PMMA is a non-resorbable polymeric material. During its polymerization unreacted monomer, catalyst and low molecular weight oligomers become entrapped in the polymer. These chemicals have the potential to leach out of the material resulting in localized cytotoxic and immunological responses. PMMA polymerization has a high exothermicity that can potentially cause heat necrosis. This exothermicity also limits the ability of PMMA to incorporate any pharmacological or chemotherapeutic agents. PMMA leakage from a defect can result in very serious complications including compression of adjacent structures (requiring further surgery) and/or embolism.

As indicated above, there are a number of calcium salt based "injectable void fillers" in the prior art. However moldable pastes also come under this heading. Putties and pastes require surgical placement of a defect. In practice this requires the defect to be surgically revealed. Unfortunately the larger the defect the larger the surgical wound site (US-patent 2005136038). Another major complication with calcium salts is their requirement to for setting in vivo. This is usually achieved by chemical reaction. Thus any biologics and pharmaceutics incorporated in the filler such as cells and pharmacological agents can potentially be damaged. Furthermore, if the filler is too "fluid" it can leak out of the defect into adjacent spaces leading to compression of structures. Leakage from defects proximal to joints can potentially impair the joints function.

Requirements for a calcium salt composition intended for delivery via the percutaneous route have previously been detailed in WO 95/21634. These include that the material should be sterilizable, must be non-toxic in vitro, the rheology must be such that it permits injection, it must be easy to use and it must have a strong mineralization front.

Thus, a strong need exists for new injectable bone void fillers which can be sterilized, show a low potential toxicity and a low tendency for leakage, are biodegradable, have a rheology that permits injection and are easy to use.

Therefore, it is an object of the present invention to provide new injectable void bone fillers for injection into osseous defects or voids resulting, for example, from osteoporosis, surgery, bone cysts, tumor removal or traumatic bone injury.

SUMMARY OF THE INVENTION

The present invention relates to a micro-porous injectable fully resorbable fibrin-based composition as bone void filler, which is resorbed and replaced with bone during the healing process. Said bone void filler composition of the present application exhibits characteristics, such as mechanical properties typically seen in elastomers and mechanical stability, superior to fibrin alone. According to the present invention, a variety of properties of said bone void filler can be effectively fine-tuned by adjusting type and content of the particles as well as of the plasticizer contained in said bone void filler composition.

DETAILED DESCRIPTION OF THE INVENTION

One aspect of the present invention relates to a multi-component system for an injectable bone void filler composition, comprising:
- component (a) comprising fibrinogen;
- component (b) comprising thrombin;
- component (c) comprising at least one plasticizer; and
- component (d) comprising particles having a diameter of about 200 µm or less.

According to one embodiment of the present invention the components (a) to (d) of the multi-component system as defined above are each present in solution, wherein at least component (a) is spatially separated from component (b).

The multi-component system for an injectable bone void filler composition as defined above may further include any other component suitable for e.g. augmenting, strengthening, supporting, repairing, rebuilding, healing or filling a bone, such as osteoinductive agents, growth factors, chemotherapeutic or pharmacological agents, biologically active agents, hardening and/or adhesive compounds and mineral additives. These compounds may be contained in any of the components (a) to (d) of the multi-component system according to the present invention or may be comprised as extra components.

According to one example of the present invention, the fibrinogen component (a) of the multi-component system as defined above may further comprise one or more of extracellular matrix proteins, for example fibronectin, cellular associated proteins, other plasma derived proteins, for example blood clotting factor XIII (FXIII) and proteases, and protease inhibitors, and mixtures thereof. The fibrinogen solution according to the present invention may also include any additive which is comprised in the state of the art for scientific and/or commercially available fibrinogen compositions, for example commercially available fibrinogen solutions.

The term "fibrinogen" includes not only fibrinogen per se, but also any clot-forming substance, such as clot-forming derivatives of fibrinogen, for example "fibrin1".

The amount of fibrinogen in component (a) of the multi-component system ranges for example from about 10 to about 200 mg/ml, such as from about 30 to about 150 mg/ml or from about 75 to about 115 mg/ml.

The thrombin component (b) of the multi-component system according to the present invention, may further comprise additional compounds known in the art as well as one or both of the components (c) and (d), particularly the plasticizer component (c). There is no specific limitation in respect to the used thrombin amount. In one example of the present invention, the amount of thrombin in said thrombin component (b) is such that it is at least about 1 IU/ml in the final clotted composition, such as about 30 IU/ml.

The term "thrombin" includes not only thrombin per se, but also any gelation-inducing or clotting-inducing agent for component (a), for example a physiologically acceptable alkaline buffer system.

The term "plasticizer", as used herein, includes any suitable substance useful in modifying the properties of the final clotted composition, for example the viscosity, the elastomeric behaviour or the mechanical stability. In one embodiment of the present invention, the plasticizer of the multi-component system as defined above has a low osmolality and allows fibrin assembly to occur at an appropriate extent.

In one example of the present invention, the suitable plasticizer of the multi-component system according to the present invention comprises at least one biodegradable, water soluble organic compound.

As used herein, the expression "biodegradable, water soluble organic compound" further includes all compounds which can be degraded in a biological environment and are at least sufficiently soluble in water, for example at temperatures in the range from about 10 to about 40° C.

Examples of the plasticizer of the multi-component system as defined above are selected from the group consisting of water-soluble contrast agents, polyethylene glycols, polyvalent alcohols such as glycerol, mono-, di-, tri- and polysaccharides, and any combination thereof.

In one example of the present invention, the suitable contrast agent of the multi-component system according to the present invention comprises at least one iodine containing organic compound. In a further example of the present invention, organic compounds containing rare earth elements such as gadolinium can be used.

As used herein, the term "iodine containing organic compound" includes all compounds which contain at least one iodine atom and/or iodine ion, bonded either physically or chemically, for example covalently or coordinatively. The same definition applies mutatis mutandis to the above-mentioned organic compound containing rare earth elements.

Examples of contrast agents, without being limited thereto, are diatrizoate (meglumine), iodecol, iodixanol, iofratol, iogulamide, iohexol, iomeprol, iopamidol, iopromide, iotrol, ioversol, ioxaglate and metrizamide and mixtures thereof.

According to one example of the present invention, the amount of plasticizer in component (c) is such that it ranges from about 10 to about 80% w/v, such as from about 15 to about 60% w/v or from about 20 to about 40% w/v, in the final clotted composition.

The term "particle" includes any type of particle shape or form known in the art, for example spherical, angular or hollow.

In one embodiment of the present invention, the particles of the multi-component system according to the present invention are biodegradable and/or biocompatible, non-toxic, non-watersoluble, inorganic and/or organic. The particles comprise, for example, substances selected from the group consisting of calcium salts such as tricalcium phosphate, alpha-tricalcium phosphate, beta-tricalcium phosphate, calcium phosphate, a polymorph of calcium phosphate, hydroxyapatite, calcium carbonate, calcium sulfate, polymeric compounds such as polylactide, polyglycolide, polycaprolactone, polytrimethylene carbonate, polyethylene glycol and random or ordered copolymers thereof, biodegradable or biocompatible glasses and ceramics and any combination thereof. In one example, the particles are selected from the group consisting of tricalcium phosphate, alpha-tricalcium phosphate, beta-tricalcium phosphate and calcium phosphate and mixtures thereof, having a Ca/P ratio in the range of about 1.5 to about 2. The particles of the present invention further include all commercially available compounds and/or mixtures known in the art to be used within the meaning of component (d). According to another example, said particles of the multi-component system of the present invention have a diameter of less than about 100 µm, for example less than about 50 µm. In one specific example of the present invention the amount of the particles in component (d) ranges from about 1 to about 50% w/w, such as from about 10 to about 45% w/w or from about 30 to about 40% w/w in respect to the final clotted composition.

According to one embodiment of the present invention, the amount of fibrinogen in component (a) of the multi-component system as defined above ranges from about 10 to about 200 mg/ml, the amount of thrombin in component (b) is such that it is at least about 1 IU/ml in the final clotted composition, the amount of plasticizer contained in component (c) is such that it ranges from about 10 to about 80% w/v in the final clotted composition, and the amount of the particles in component (d) ranges from about 1 to about 50% w/w in respect to the final clotted composition.

According to a specific example of the present invention, the amount of fibrinogen in component (a) of the multi-component system as defined above ranges from about 75 to about 115 mg/ml, the amount of thrombin in component (b) is such that it ranges from about 25 IU/ml to about 50 IU/ml in the final clotted composition, the amount of plasticizer contained in component (c) is such that it ranges from about 30 to about 50% w/v in the final clotted composition, and the amount of the particles in component (d) ranges from about 30 to about 40% w/w in respect to the final clotted composition.

In another embodiment of the present invention, the multi-component system for an injectable bone void filler composition, comprises:

component (a) comprising fibrinogen;
component (b) comprising thrombin;
component (c) comprising at least one plasticizer; and
component (d) comprising particles having a diameter of about 200 μm or less;

wherein one or more or all of the components (a) to (d) are present in a solid form.

The multi-component system according to the present invention may contain the components either in form of a solution or of a dispersion or of a solid, for example as a lyophilisate, or any combination thereof. Further, the components in said multi-component system may be present in containers suitable for storage, transportation or use of said multi-component system. The containers usable in the multi-component system according to the present invention are not limited in any way but include containers of any size, material or shape, for example vials or syringes.

Moreover, the components of said multi-component system may for example be contained in different containers or may be present in the same container in any combination, for example as a combination of components (b) and (c) in one container and of components (a) and (d) each in different containers.

According to the present invention, the containers may for example contain one or more components as a solid, as well as a solvent separated from said components by a separation means in said container, wherein a solution of the respective one or more components can be prepared by breaking or removing said separation means. The components (a) to (d) of the multi-component system of the present invention may be also present as a ready-to-use mixture.

Moreover, said components (a) to (d) present in one or more containers may also be part of a kit, comprising the multi-component system as defined above. The kit may further comprise any additional compound usable in the multi-component system of the present invention, for example auxiliary agents, buffer salts or buffer solutions. The kit as defined above may also contain means for mixing the components, for example syringes, Luer adapters, tubes, extra containers, etc.

Another aspect of the present invention relates to an injectable bone void filler composition, comprising:

component (a) comprising fibrin;
component (b) comprising thrombin;
component (c) comprising at least one plasticizer; and
component (d) comprising particles having a diameter of about 200 μm or less.

According to one example of the present invention, the injectable bone void filler composition is prepared from the multi-component system as defined above, for example by mixing the components of said multi-component system together and/or homogenizing said components. The preparation of the injectable bone void filler composition can be carried out at any suitable temperature, such as in the range from about 18 to about 37° C., for example at 25° C.

Moreover, the injectable bone void filler composition as defined above may further include any other component suitable for e.g. augmenting, strengthening, supporting, repairing, rebuilding, healing or filling a bone, such as osteoinductive agents, growth factors, chemotherapeutic or pharmacological agents, biologically active agents, hardening and/or adhesive compounds and mineral additives. These compounds and/or agents can be chemically attached to the matrix, adsorbed on the particulate component, for example on calcium salt containing particles, trapped in the fibrin matrix or contained as a free molecule/drug particle, for example a powder.

The components (b) to (d) of the injectable bone void filler composition according to the present invention are the same as defined for the multi-component system characterized above.

The term "fibrin" does not only refer to fully coagulated fibrinogen but further includes any mixture of fibrin and fibrinogen which may occur during formation of fibrin from fibrinogen using thrombin and, thus, includes any ratio of fibrinogen/fibrin and any grade of gelation and/or clotting conceivable as long as it has no negative impact on the final composition injected into the non-mineralized or hollow portion of a bone. The fibrin component (a) of the injectable bone void filler composition of the present invention further includes fibrin with only a small amount of fibrinogen or without any fibrinogen left in said fibrin. Moreover, the term "fibrin" further includes any partly or fully gelled or clotted form of component (a) as defined above.

According to one example of the present invention, the amount of fibrin in said fibrin component (a) of the injectable bone void filler composition as defined above ranges from about 5 to about 100 mg/ml, such as from about 15 to 65 mg/ml or from about 30 to 65 mg/ml in the final clotted composition.

According to another example, the amount of fibrin in said fibrin component (a) of the injectable bone void filler composition of the present invention ranges from about 5 to about 100 mg/ml in the final clotted composition, the amount of thrombin in component (b) is at least about 1 IU/ml in the final clotted composition, the amount of plasticizer contained in component (c) ranges from about 10 to about 80% w/v in the final clotted composition, and the amount of particles in component (d) ranges from about 1 to about 50% w/w in respect to the final clotted composition.

According to the present invention, the injectable bone void filler composition as defined above is in a gelled or clotted state and has a viscosity suitable for injecting into a non-mineralized or hollow portion of a bone, and may be applied in a pre-clotted liquid, gelled or clotted state.

As used herein, the term "gelled" means any state of elevated viscosity when compared to the initial state. This can be observed for example in the formation of fibrin from fibrinogen or in a finely dispersed system of at least one solid phase and at least one liquid phase, such as a colloid. Further, the term "gelled" includes all states of gelation known in the art.

The term "clotted" means, for example, a gel comprising fibrin and includes any kind of coagulation state known in the art.

According to the present invention, the viscosity of the injectable bone void filler composition depends on the application, i.e. the bone disorder to be treated, and is adjusted within the common knowledge of a person skilled in the art. For example, an injectable composition for filling bone cysts contains a lower fibrin amount and/or a lower amount of calcium salt-containing particles. An injectable composition for replacing non-mineralized portions of the bone contains a higher fibrin amount and/or a higher amount of calcium salt-containing particles. According to one example of the present invention, the viscosity of the bone void filler composition of the present invention ranges from about 100 mPas to about 1000 Pas.

Another aspect of the present invention, relates to a method of filling a void in a bone in a patient suffering from a bone disorder, comprising injecting the injectable bone void filler composition as characterized above, into a non-mineralized or hollow portion of said bone.

As used herein, the term "patient" means a subject suffering from a bone disorder and includes mammals, particularly human beings.

The method of filling a void in a bone as defined above is not limited to a certain mode of treatment and includes any kind of injection technique, for example percutaneous injection. According to a specific example of the present invention, the method for filling a void in a bone as defined above is percutaneous bone augmentation and comprises vertebroplasty and kyphoplasty.

Moreover, the method of filling a void in a bone according to the present invention can be used for strengthening, supporting, repairing, rebuilding, healing, augmenting or filling a bone, for example a bone in a human suffering from a bone disorder including trauma or fracture. Another field of application is, for example, spinal fusion.

Examples of such bone disorders are osteoporosis, osteoporotic bone fractures, traumatic fractures of any type of bone, benign and malignant lesions and surgically created defects.

The bone void filler composition according to the present invention advantageously meets all the requirements for a composition usable in the treatment of osseous defects or voids. The bone void filler composition is sterilizable, is easy to use and the rheology of it does permit injection. Surprisingly, If calcium salts are used as the particulate component in the composition it is possible to achieve a strong mineralization front which is highly beneficial in the healing process of a bone disorder as described above. Furthermore, the bone void filler of the present invention is fully resorbable and is replaced with bone during the healing process. Advantageously, said bone void filler composition shows substantially no exothermicity and exhibits mechanical properties, such as mechanical behaviour typically seen in elastomers, superior to fibrin alone. All essential properties, for example viscosity, mechanical stability, resorbability, etc., can be surprisingly effectively fine-tuned by adjusting type and content of the particles as well as of the plasticizer contained in said bone void filler composition, within the claimed scope of protection.

Figure 1:
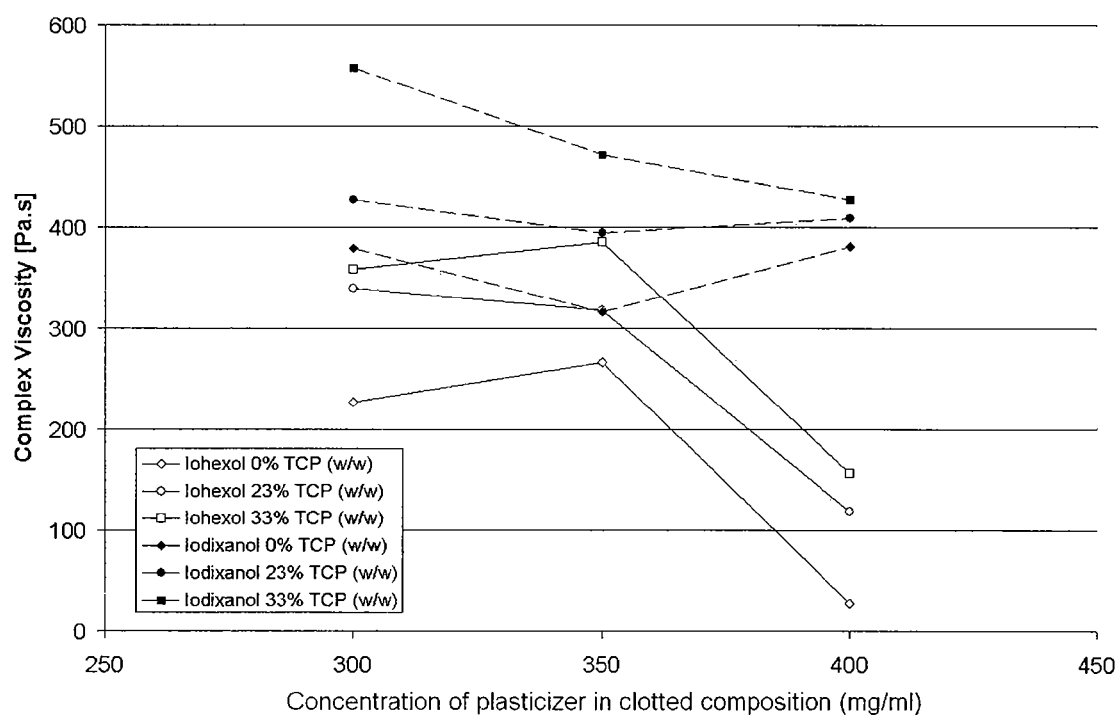
FIG. 1: Rheological analysis of compositions containing 30% of the plasticizer iodixanol and 75 IU/ml thrombin. The effect of increasing calcium phosphate in the composition is clearly seen. Complex viscosity is plotted on a linear scale.

The present invention will be further illustrated in the following examples, without any limitation thereto.

EXAMPLES

Example 1

Preparation of Bone Void Filler Composition Containing Fibrin, Glycerol and Calcium Phosphate Materials:

| | |
|---|---|
| Fibrin sealant solution | Freeze dried fibrinogen powder reconstituted with aprotinin solution to a total clottable protein concentration of 91 mg/ml. |
| Iodixanol | 5-[acetyl-[3-[acetyl-[3,5-bis(2,3-dihydroxypropylcarbamoyl)-2,4,6-triiodo-phenyl]-amino]-2-hydroxy-propyl]-amino]-N,N'-bis(2,3-dihydroxypropyl)-2,4,6-triiodo-benzene-1,3-dicarboxamide |
| Iohexol | 5-(acetyl-(2,3-dihydroxypropyl)amino)-N,N'-bis(2,3-dihydroxypropyl)-2,4,6-triiodo-benzene-1,3-dicarboxamide |
| Particles | Tricalcium phosphate particles (TCP), 35 µm, spherical (Plasma Biotal, Derby UK) |
| Thrombin 500 IU/ml | Freeze dried thrombin powder reconstituted with 5 ml of thrombin buffer, to a concentration of 500 IU/ml. |
| Thrombin Buffer | 40 mM $CaCl_2$ in $H_2O$ |

A 40% plasticizer (gycerol) and 10 IU/ml thrombin solution is prepared in a thrombin dilution buffer (40 mM $CaCl_2$ in double distilled water). The solution is then homogenised. The solution is centrifuged to remove bubbles and sterilised by filtering through a 0.22 µm filter. The fibrinogen is mixed with thrombin/plasticizer in a 1:1 ratio (therefore the plasticizer concentration in the gelled clot is halved). For this 2 ml of the glycerol/thrombin solution is transferred to a 5 ml syringe. 2 ml of fibrinogen (91 mg/ml) is transferred to a separate 5 ml syringe. The particles (ca. 2 µm) are incorporated as percentage weight of the final clot volume (w/v). These are weighed and placed into another 5 ml syringe.

The syringes containing the particles and the thrombin are connected via a Luer adapter and the thrombin/glycerol and particles homogenised by transferring the contents from syringe to syringe thoroughly.

The syringes containing the thrombin/glycerol/particles and the fibrinogen are connected via a Luer adapter and the contents homogenised.

The material remains liquid for approximately 1 minute. During this time it can be injected into the defect or alternatively after a few minutes it can be delivered as a pre-formed gel.

Example 2

Preparation of Bone Void Filler Composition Containing Fibrin, a Contrast Agent and Calcium Phosphate Either an 80% or a 60% plasticizer (contrast agents iodixanol or iohexol) and a 75 IU/ml thrombin solution is prepared in a thrombin dilution buffer (40 mM $CaCl_2$ in double distilled water) The solution is then homogenised. The solution is centrifuged to remove bubbles and sterilised by filtering through a 0.22 µm filter. The fibrinogen is mixed with thrombin/contrast agent (CA) in a 1:1 ratio (therefore the plasticizer concentration in the gelled clot is halved to either 40 or 30%). For this 2 ml of the thrombin/contrast agent solution is transferred to a 5 ml syringe. 2 ml of fibrinogen (91 mg/ml) is transferred to a separate 5 ml syringe. The particles (ca. 2 µm) are incorporated as percentage weight of the final clot volume (w/v). These are weighed and placed into another 5 ml syringe.

The syringes containing the particles and the thrombin are connected via a Luer adapter and the thrombin/CA and particles homogenised by transferring the contents from syringe to syringe thoroughly.

The syringes containing the thrombin/CA/particles and the fibrinogen are connected via a Luer adapter and the contents homogenised.

The material remains liquid for approximately 1 minute during this time it can be injected into the defect or alternatively after a few minutes it can be delivered as a pre-formed gel.

Figure 2:
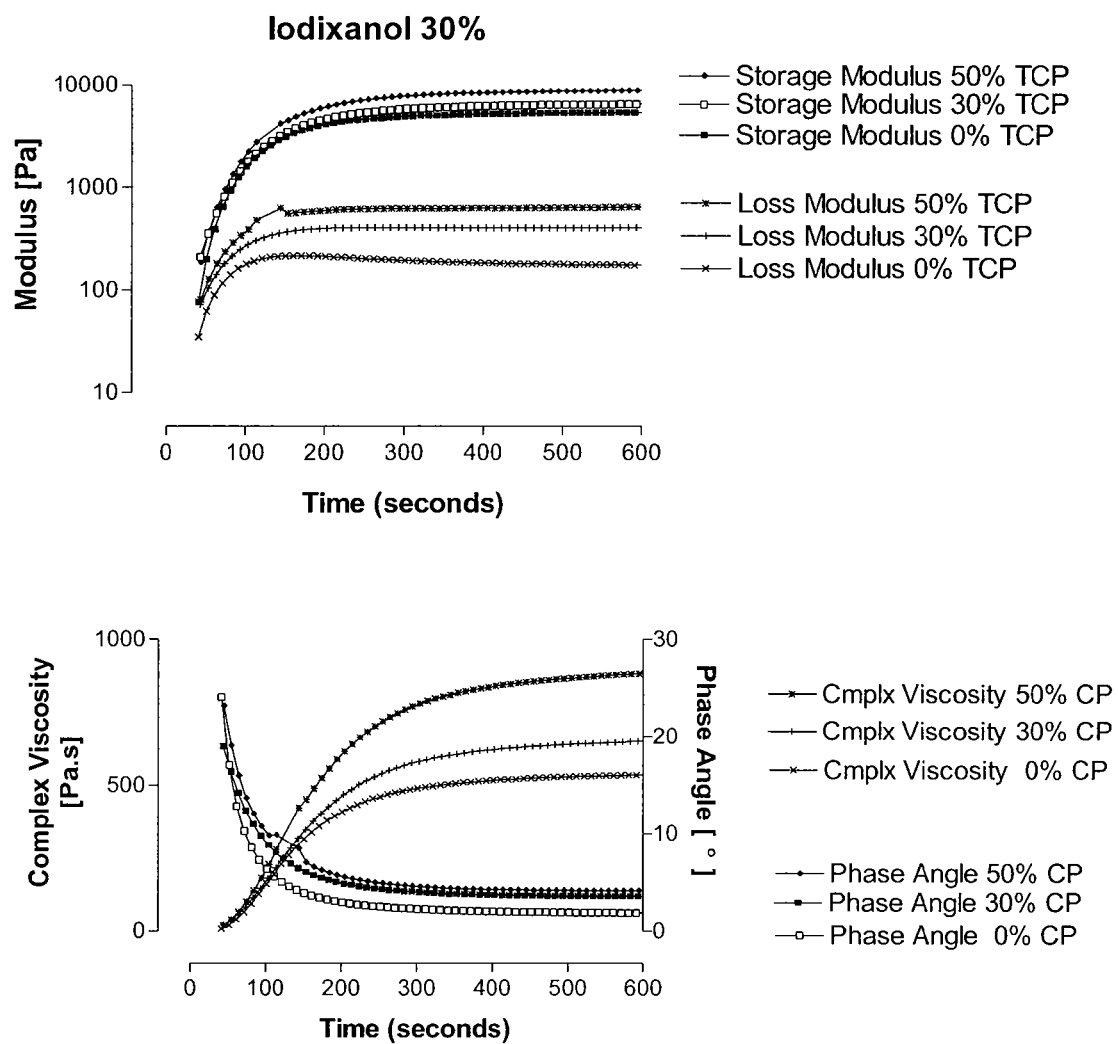
FIG. 2: Differences in complex viscosities as a result of increasing concentration of plasticizer and/or the particulate content.

The viscosities of the respective clots with different concentrations of contrast agents and of TCP can be taken from FIG. 1. Rheological data of compositions containing of iodixanol as plasticizer and increasing amounts of calcium salts can be taken from FIG. 2.

Example 3

Use of the Bone Void Filler for Filling a Bone Void in the Long Bone of a Rabbit The injectable bone void filler was prepared according to Example 2.

Figure 3:
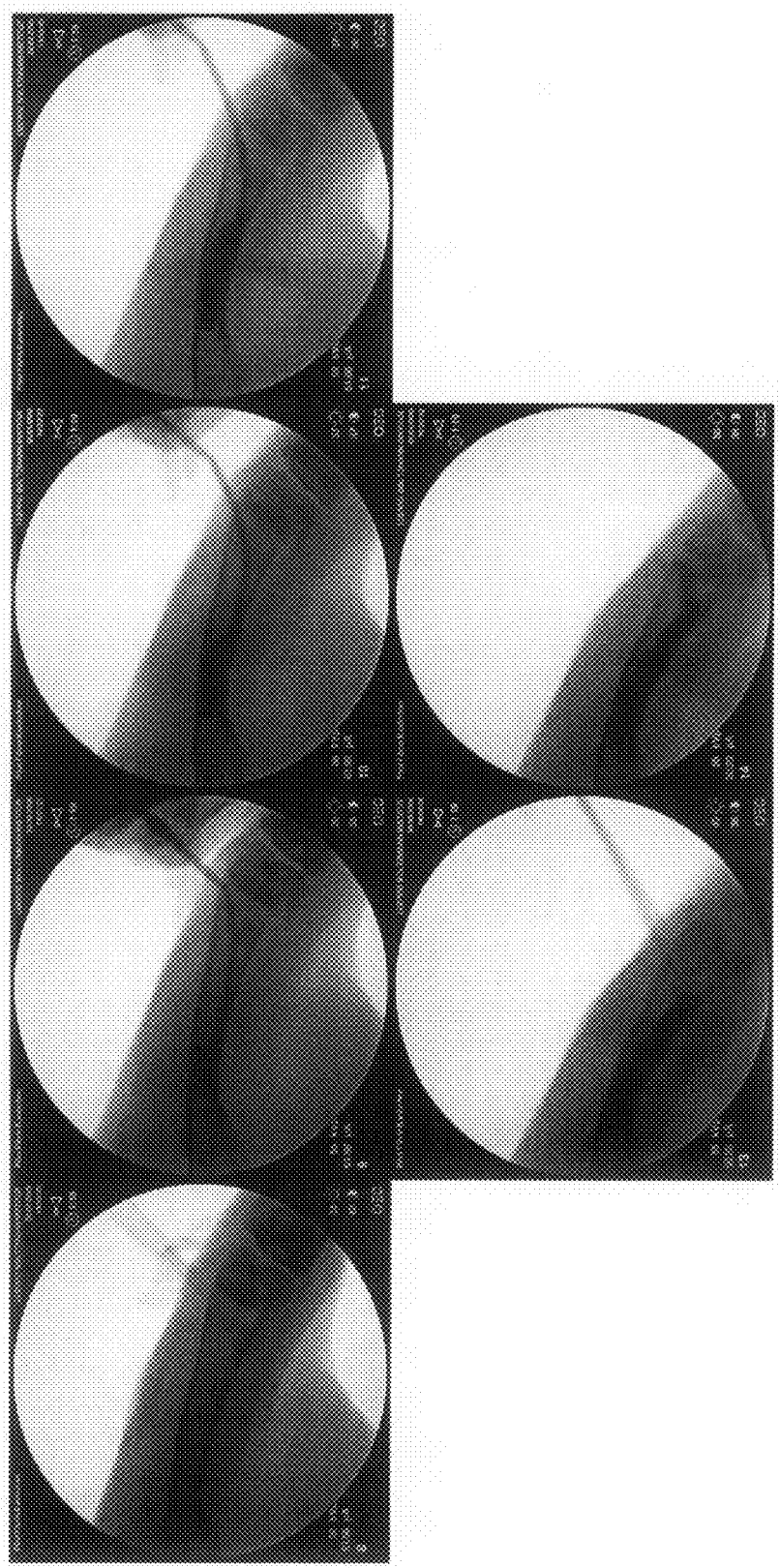
FIG. 3: The delivery of the injectable bone void filler according to the present invention into a bone void in the long bone of a rabbit. The catheter is inserted and the void is filled. Following the procedure, the catheter is easily removed.

The bone marrow is removed from a rabbit long bone to form a hollow bone. Then the injectable bone void filler is injected into the hollow bone using a plastic catheter. After the procedure, the plastic catheter is easily removed from the hollow portion of said bone (cf. FIG. 3).

Example 4

In Vivo Studies of the Injectable Bone Void Filler Composition in Sheep

The medial fascia of the tibia shaft is excised and the tibia is exposed. A plate is contoured to the shaft and fixed to the bone using screws. The plate is removed again and a standardized 1 cm full thickness defect is created. The segment is removed, the plate is repositioned and the screws are reinserted. Thereafter, the injectable bone augmentation composition is filled into the defect and the wound is closed by suture.

The animals are followed up for 4, 8 and 12 weeks (X-ray evaluation). At the 12 weeks timepoint the animals are sacrificed and the tibia is extracted for final analysis (µCT and histology).

The bone void filler composition and the resulting clots according to the present invention exhibited excellent properties.

We claim:

1. A multi-component system for preparing an injectable bone void filler composition, the system comprising:
   component (a) comprising fibrinogen;
   component (b) comprising thrombin; and
   component (c) comprising a plasticizer selected from the group consisting of iodixanol and iohexol;
      wherein the plasticizer is present in an amount within a range from 300 mg/ml to 400 mg/ml of the composition.

2. The multi-component system according to claim 1, wherein the components (a) to (c) are present in solution and at least component (a) is spatially separated from component (b).

3. The multicomponent system according to claim 1, further comprising particles having a diameter of 200 µm or less, wherein the amount of the particles ranges from about 10 to about 45% w/w in respect to the composition, and wherein the particles comprise substances selected from the group consisting of calcium salts, polymeric compounds, biodegradable or biocompatible glasses and ceramics.

4. The multi-component system according to claim 3, wherein the substances are selected from the group consisting of tricalcium phosphate, alpha-tricalcium phosphate, beta-tricalcium phosphate, calcium phosphate, a polymorph of calcium phosphate, hydroxyapatite, calcium carbonate, calcium sulfate, polyactide, polyglycolide, polycaprolactone, polytrimethylene carbonate, polyethylene glycol, and any combination thereof.

5. The multi-component system according to claim 4, wherein the substances are selected from the group consisting of tricalcium phosphate, alpha-tricalcium phosphate, beta-tricalcium phosphate and calcium phosphate and mixtures thereof, and/or wherein said particles have a Ca/P ratio in the range from about 1.5 to about 2.

6. The multi-component system according to claim 1, wherein the amount of fibrinogen in component (a) ranges from about 10 to about 200 mg/ml.

7. The multi-component system according to claim 1, wherein the amount of thrombin in component (b) is such that it is at least about 1 IU/ml in the composition.

8. The multi-component system according to claim 1, wherein the amount of fibrinogen in component (a) ranges from about 10 to about 200 mg/ml, and the amount of thrombin in component (b) is such that it is at least 1 IU/ml in the composition.

9. The multi-component system according to claim 1, further comprising particles having a diameter of less than 100 µm, wherein the amount of the particles ranges from about 10 to about 45% w/w in respect to the composition.

10. The multi-component system according to claim 1, further comprising particles having a diameter of less than 50 µm, wherein the amount of the particles ranges from about 10 to about 45% w/w in respect to the composition.

11. A method of filling a void in a bone in a patient suffering from a bone disorder, comprising injecting the injectable bone void filler composition into a non-mineralized or hollow portion of said bone, wherein the injectable bone void filler composition comprises:
   component (a) comprising fibrin;
   component (b) comprising thrombin; and
   component (c) comprising a plasticizer selected from the group consisting of iodixanol and iohexol, wherein:
      the amount of the plasticizer is within a range from 300 mg/ml to 400 mg/ml of the composition.

12. The method of filling a void in a bone according to claim 11, wherein the bone disorder is selected from the group consisting of osteoporosis, osteoporotic bone fractures, traumatic fractures of any type of bone, benign and malignant lesions and surgically created defects.

13. The multi-component system according to claim 1, further comprising particles having a diameter of 200 µm or less, wherein the amount of the particles ranges from about 30 to about 40% w/w in respect to the composition.

14. The system according to claim 1, wherein the plasticizer comprises iodixanol in an amount from between about 300 mg/ml to about 400 mg/ml of the composition.

15. The system according to claim 1, wherein the plasticizer comprises iohexol in an amount from between about 300 mg/ml to about 400 mg/ml of the composition.

16. The method of filling a void in a bone according to claim 11, wherein the injectable bone void composition further comprises particles having a diameter of 200 μm or less, wherein:
   the amount of the particles ranges from about 10 to about 45% w/w in respect to the composition, and
   the particles are selected from the group consisting of tricalcium phosphate, alpha-tricalcium phosphate, beta-tricalcium phosphate, calcium phosphate, a polymorph of calcium phosphate, hydroxyapatite, calcium carbonate, calcium sulfate, polyactide, polyglycolide, polycaprolactone, polytrimethylene carbonate, polyethylene glycol, and any combination thereof.

17. The method of filling a void in a bone according to claim 16, wherein the particles are selected from the group consisting of tricalcium phosphate, alpha-tricalcium phosphate, beta-tricalcium phosphate and calcium phosphate, and mixtures thereof, and/or wherein said particles have a Ca/P ratio in the range of about 1.5 to about 2.

18. The method of filling a void in a bone according to claim 11, wherein the amount of thrombin in component (b) is at least 1 IU/ml in the composition.

19. The method of filling a void in a bone according to claim 11, further comprising particles having a diameter of less than 100 μm, wherein the amount of the particles ranges from about 10 to about 45% w/w in respect to the composition.

20. The method of filling a void in a bone according to claim 11, further comprising particles having a diameter of less than 50 μm, wherein the amount of the particles ranges from about 10 to about 45% w/w in respect to the composition.

21. The method of filling a void in a bone according to claim 11, wherein the composition is in a gelled or clotted state and has a viscosity suitable for injecting into a non-mineralized or hollow portion of a bone.

22. The method of filling a void in a bone according to claim 11, wherein the plasticizer comprises iodixanol in an amount from between about 300 mg/ml to about 400 mg/ml of the composition.

23. The method of filling a void in a bone according to claim 11, wherein the plasticizer comprises iohexol in an amount from between about 300 mg/ml to about 400 mg/ml of the composition.

24. A method of filling a void in a bone in a patient suffering from a bone disorder, comprising injecting the injectable bone void filler composition into a non-mineralized or hollow portion of said bone, wherein the injectable bone composition is prepared from a multi-component system comprising:
   component (a) comprising fibrinogen;
   component (b) comprising thrombin; and
   component (c) comprising a plasticizer selected from the group consisting of iodixanol and iohexol; wherein:
   the amount of the plasticizer is within a range from 300 mg/ml to 400 mg/ml of the composition.

25. The method filling a void in a bone according to claim 24, wherein one or more of the components (a) to (c) are present in a solid form.

26. The method filling a void in a bone according to claim 24, wherein the bone disorder is selected from the group consisting of osteoporosis, osteoporotic bone fractures, traumatic fractures of any type of bone, benign and malignant lesions and surgically created defects.

27. The method filling a void in a bone according to claim 25, wherein the bone disorder is selected from the group consisting of osteoporosis, osteoporotic bone fractures, traumatic fractures of any type of bone, benign and malignant lesions and surgically created defects.

28. The method filling a void in a bone according to claim 24, wherein the multi-component system further comprises particles having a diameter of 200 μm or less, and the amount of the particles ranges from about 30 to about 40% w/w in respect to the composition.

29. The method filling a void in a bone according to claim 24, wherein the multi-component system further comprises particles having a diameter of 100 μm or less, and the amount of the particles ranges from about 30 to about 40% w/w in respect to the composition.

* * * * *

UNITED STATES PATENT AND TRADEMARK OFFICE
CERTIFICATE OF CORRECTION

PATENT NO. : 9,248,215 B2  
APPLICATION NO. : 11/736500  
DATED : February 2, 2016  
INVENTOR(S) : Barry et al.

Page 1 of 1

It is certified that error appears in the above-identified patent and that said Letters Patent is hereby corrected as shown below:

In the Claims:

In Column 12, line 16, Claim 25: please insert --of-- after "method".

In Column 12, line 19, Claim 26: please insert --of-- after "method".

In Column 12, line 24, Claim 27: please insert --of-- after "method".

In Column 12, line 29, Claim 28: please insert --of-- after "method".

In Column 12, line 34, Claim 29: please insert --of-- after "method".

Signed and Sealed this  
Thirty-first Day of May, 2016

Michelle K. Lee  
*Director of the United States Patent and Trademark Office*